(12) United States Patent
Jahn

(10) Patent No.: US 11,123,162 B2
(45) Date of Patent: Sep. 21, 2021

(54) METHOD FOR PRODUCING AN ANATOMICAL DENTAL IMPLANT

(71) Applicant: NT-TRADING GMBH & CO. KG, Karlsruhe (DE)

(72) Inventor: Dirk Jahn, Weyher (DE)

(73) Assignee: NT-TRADING GMBH & CO. KG, Karlsruhe (DE)

( * ) Notice: Subject to any disclaimer, the term of this patent is extended or adjusted under 35 U.S.C. 154(b) by 401 days.

(21) Appl. No.: 15/752,295

(22) PCT Filed: Aug. 10, 2016

(86) PCT No.: PCT/EP2016/069054
§ 371 (c)(1),
(2) Date: Feb. 13, 2018

(87) PCT Pub. No.: WO2017/029168
PCT Pub. Date: Feb. 23, 2017

(65) Prior Publication Data
US 2018/0235739 A1     Aug. 23, 2018

(30) Foreign Application Priority Data

Aug. 14, 2015   (DE) ..................... 10 2015 215 587.0

(51) Int. Cl.
*A61C 13/00*     (2006.01)
*A61B 6/03*      (2006.01)
(Continued)

(52) U.S. Cl.
CPC .......... *A61C 13/0004* (2013.01); *A61B 6/032* (2013.01); *A61C 8/0036* (2013.01); *A61C 13/0013* (2013.01); *A61C 13/0019* (2013.01); *A61B 6/14* (2013.01); *A61F 2/2803* (2013.01); *A61F 2002/2835* (2013.01);
(Continued)

(58) Field of Classification Search
CPC ............ A61C 13/0004; A61C 13/0013; A61C 13/0019; A61C 8/0036
See application file for complete search history.

(56) References Cited

U.S. PATENT DOCUMENTS 8,359,114 B2   1/2013  Steingart et al.
8,485,820 B1   7/2013  Ali
(Continued)

FOREIGN PATENT DOCUMENTS

CN   102083387 A   6/2011
CN   202724012 U   2/2013
(Continued)

OTHER PUBLICATIONS

International Search Report with English translation issued in Application No. PCT/EP2016/069054 dated Oct. 17, 2016 (7 pages).
(Continued)

*Primary Examiner* — Nicholas D Lucchesi
(74) *Attorney, Agent, or Firm* — Flynn Thiel, P.C.

(57) ABSTRACT

A method for producing a bone replacement, a cavity or a bone being detected in a fully automated manner and the bone replacement being produced based on the detection also in a fully automated manner. It is also possible to produce information in relation to medical instruments or navigation information in a fully automated manner.

28 Claims, 2 Drawing Sheets

(51) Int. Cl.
*A61C 8/00* (2006.01)
*B33Y 10/00* (2015.01)
*B33Y 80/00* (2015.01)
*A61B 6/14* (2006.01)
*A61F 2/28* (2006.01)

(52) U.S. Cl.
CPC ....... *A61F 2002/2889* (2013.01); *B33Y 10/00* (2014.12); *B33Y 80/00* (2014.12)

(56) References Cited

U.S. PATENT DOCUMENTS

| | | | | |
|---|---|---|---|---|
| 2004/0243481 | A1* | 12/2004 | Bradbury | A61C 13/0004 705/26.1 |
| 2009/0287332 | A1 | 11/2009 | Adusumilli et al. | |
| 2009/0325128 | A1* | 12/2009 | Holzner | A61C 13/0004 433/201.1 |
| 2010/0203478 | A1* | 8/2010 | Rubbert | A61C 9/0053 433/212.1 |
| 2012/0251980 | A1 | 10/2012 | Bassett et al. | |

FOREIGN PATENT DOCUMENTS

| | | |
|---|---|---|
| CN | 103997985 A | 8/2014 |
| JP | 2015507491 A | 3/2015 |
| RU | 2 494 700 C2 | 7/2011 |
| WO | 2008086978 A1 | 7/2008 |
| WO | 2012052482 A1 | 4/2012 |
| WO | WO 2013/096592 A1 | 6/2013 |

OTHER PUBLICATIONS

Written Opinion of International Searching Authority issued in Application No. PCT/EP2016/069054 dated Oct. 17, 2016 (6 pages).
Office Action of German Patent Office issued in Application No. 10 2015 215 587.0 dated Mar. 15, 2016 (8 pages).
Search Report and Office Action of Russian Patent Office issued in Russian Application No. 2018105850/14 with English translation dated Jan. 21, 2019 (15 pages).
Chinese Examination Report issued from the Chinese Patent Office corresponding to Chinese Application No. 201680048348.5 dated Feb. 3, 2020 (10 pages).
Notice of Reasons for Rejection with English Translation, issued in corresponding Japanese Application No. 2018-507611 dated Jan. 21, 2020 (9 pages).

* cited by examiner

METHOD FOR PRODUCING AN ANATOMICAL DENTAL IMPLANT

BACKGROUND AND PRIOR ART

The invention relates to a method for producing a bone replacement and to a bone replacement.

Bone replacements can be inserted into human or animal bones in order to replace a piece of bone that is no longer present or should be removed. By way of example, such a replacement may become necessary if a tooth root, on account of disease, is destroyed, not disposed or otherwise defective, or if part of a bone was knocked out on account of an accident.

As a rule, it is necessary, for bone replacements, to establish a fit that is as good as possible between a bone replacement and a cavity in which the bone replacement should be received. This facilitates a fit without play and a good seat in the long-term.

Known methods for producing a bone replacement are typically based on taking a print of the cavity using a mass which can solidify in the cavity and producing the bone replacement on the basis thereof. However, this is accompanied by the disadvantage that an intervention has to be undertaken on the patient for this purpose and that, moreover, the formation of such a print is only possible once the cavity is free and accessible from the outside. By way of example, the production of a replacement for a tooth root is consequently only possible once the tooth root has been removed from the jaw. On account of the time duration connected therewith, this may constitute a significant stress on the patient. Moreover, steps to be carried out manually, in particular, produce sources of errors which may lead to errors when treating the patient.

Problem and Solution

It is therefore an object of the invention to provide a method for producing a bone replacement which, for example, facilitates a performance requiring faster or fewer interventions on the patient. Further, it is an object of the invention to provide a bone replacement which avoids disadvantages known from the prior art.

According to the invention, this is achieved by a method for producing a bone replacement and by a bone replacement.

The invention relates to a method for producing a bone replacement, wherein the method includes the following steps:

- measuring a cavity in a bone for producing initial data which are indicative for a structure of the cavity,
- producing processing data from the initial data, wherein the processing data are indicative for an intended structure of the bone replacement, and
- producing the bone replacement by automated processing using the processing data.

A far-reaching automation of the production of a bone replacement is possible by way of the method according to the invention. This can significantly reduce necessary interventions and the time required overall, representing a significant relief for the patient. In particular, the procedure of producing the bone replacement can be automated further, and so the risk of possible human errors is also minimized.

Typically, a cavity can be a hollow space, in particular a hollow space accessible from the outside, in a human or animal bone. Said cavity may have been produced deliberately, for example by means of medical instruments or by pulling a tooth, or else inadvertently such as in the case of an accident. Typically, the cavity should be refilled within the scope of the method such that, in the ideal case, the patient after their treatment no longer notices that the cavity once was originally present in the body in a non-filled state.

The structure of the cavity can be, in particular, the three-dimensional structure of the cavity. The latter can be described in a suitable manner by the initial data. By way of example, the cavity can be converted into three-dimensional pixel data. By way of example, the cavity can also be described as a vector file.

Typically, the processing data are located on a different level to the initial data. While the initial data are typically based on a measurement, the processing data are designed to be typically immediately usable for the automated production of the bone replacement. By way of example, these processing data can be NC data or CNC data, which can be used immediately in a machine tool for the automated production of the bone replacement.

According to an embodiment, the bone replacement is a bone implant or has a bone implant. Preferably, the bone implant is a jawbone implant, in particular a maxilla implant or mandible implant.

Preferably, the bone replacement is a tooth implant, an abutment and/or a dental prosthesis (artificial tooth crown) or has a tooth implant, an abutment and/or a dental prosthesis (artificial tooth crown).

Within the meaning of the present invention, the expression "abutment" should be understood to mean a connecting structure or a connecting part (mesoscopic structure) between a tooth implant and a dental prosthesis. In the case of a customized implant, the abutment serves, in particular, to compensate angular deflections of the implant, caused by the insertion, in order to be able to assume the prosthetic care in an ideal position of a tooth that is no longer present. The connection to the implant is preferably effectuated by way of screwing, the latter requiring a screw channel and a certain rigidity. By way of example, the abutment may also contain resilient and/or adhering components.

The bone replacement can be, in particular, a tooth implant with, or else without, an abutment structure. Here, the tooth implant and the abutment structure may constitute a bone replacement with an integral embodiment.

In particular, the cavity can be arranged in a mandible or in a maxilla for receiving a tooth root. Typically, such a cavity is filled with a tooth root in the healthy state. If the tooth is pulled, such a cavity is typically empty and refilled by the insertion of a tooth implant. The cavity may also extend beyond the region of a tooth root due to disease or accident, or else for prosthetic reasons.

According to a preferred embodiment, the step of measuring the cavity is carried out while a tooth root or tooth root replacement and/or a tooth or tooth replacement are situated in the cavity. This facilitates particularly little stress for the patient since the tooth only needs to be pulled once the manufacture of the bone replacement has already been completed. Thus, the patient need not mill around for days on end with a pulled tooth or a gap in the teeth arising as a result thereof in order to wait for the completion of the tooth implant.

The step of measuring the cavity is preferably carried out by means of computed tomography (CT), magnetic resonance imaging (MRI), digital video tomography (DVT) or a 3D scan. Such methods were found to be advantageous for carrying out the invention. In particular, they facilitate the exact capture and evaluation of a cavity in a bone without needing to introduce filler material or any other curing material into the cavity for this purpose. For such methods, the patient typically lies on a couch or sits or stands in a certain position, with the cavity being captured largely automatically. Moreover, it is possible to reliably preclude errors on account of air bubbles, impression material that got caught or other sources of errors.

Preferably, the initial data are converted into computer-aided design (CAD) data, with the processing data being produced on the basis of the CAD data. In particular, such CAD data can be vector data. Such CAD data facilitate the conversion of the initial data into data that can easily be processed further and also processed manually where necessary, said data having a defined structure and a defined resolution.

The processing data are preferably produced dependent on the cavity and/or a position of the cavity. This facilitates taking account of the type of cavity or a position of the cavity. By way of example, when creating the processing data, it is possible to take account of whether the cavity is situated in a maxilla or in a mandible, or take account of the position in the respective jaw or else in a completely different bone of a human or animal body. Depending thereon, it is possible to use different parameters when producing the processing data, said parameters taking account of the respective local conditions, such as the deformability of the bone or the degree to which the respective structure can be loaded.

Preferably, a finite element analysis is applied to the processing data before producing the bone replacement. In particular, this is effectuated taking account of data in respect of the maxilla, mandible, occlusion and/or bone structure. By means of such a finite element analysis, it is possible to prepare the data and adapt these in an improved manner to a specific device for producing the bone replacement. The finite element analysis particularly advantageously assists the analysis of biomechanical systems such as, for example, bones, tendons, ligaments and even blood vessels. By way of the finite element analysis as a contactless imaging method, it is possible to carry out measurements with a substantially larger dynamic range, in particular, than with conventional measurement methods.

Within the meaning of the present invention, occlusion should be understood to mean, in particular, the static and dynamic contact relationship between maxillary teeth and mandibular teeth. This contact relationship must have a harmonic/functional embodiment in order to avoid damage to the stomatognathic system. Dentally, the occlusion occurs in the region of the tooth chewing surfaces and the corresponding antagonist tooth. In the broadest sense, the chewing surface, which is shaped by cusps, slopes and fissures, can be referred to as a filled cavity.

According to a preferred embodiment, the method further has the step of optimizing and/or redesigning (renewed production of) the processing data before producing the bone replacement. Using this, it is possible to optimize the structure of the bone replacement. Optimizing and/or redesigning can be carried out both manually and in an automated fashion in each case, for example by means of a fixedly implemented algorithm. In particular, possibly occurring tension may be compensated within the scope of a redesign.

The production of the bone replacement can be effectuated by milling and/or by a generative manufacturing method, such as e.g. 3D printing.

According to a further embodiment, the bone replacement has a material or is formed from a material which is selected from the group containing metals, polymers, synthetic polymers, biopolymers (naturally occurring polymers), ceramics, cement materials and combinations, in particular mixtures or composites, thereof.

By way of example, the bone replacement can contain a material or be formed from a material which is selected from the group containing titanium, proteins, gelatin, collagen, polysaccharides, mucopolysaccharides, alginate, hyaluronic acid, polyether ketone, polyether ether ketone, phosphates, calcium phosphates, octacalcium phosphate (OCP), apatite, hydroxyapatite, phosphate ceramics, calcium phosphate ceramics, apatite ceramics, hydroxyapatite ceramics and combinations, in particular mixtures or composites, thereof.

In particular, the bone replacement may contain octacalcium phosphate (OCP) and biopolymers, such as e.g. gelatin, collagen, alginate and/or hyaluronic acid, or consist of these materials.

According to a further embodiment, the bone replacement is configured as a titanium foam, in particular a porous titanium foam, preferably an open pore titanium foam.

In particular, the bone replacement may have a microstructure, i.e. a structure with a pore dimension in the μm range (micrometer range). Preferably, the microstructure has a pore dimension <2 nm. Furthermore, the pores of the microstructure may have a honeycomb configuration.

Preferably, the bone replacement has a macroporous titanium structure, i.e. a titanium structure with a pore dimension in the μm range (micrometer range). In particular, the bone replacement may have a titanium structure with a pore dimension <2 nm. Furthermore, the pores may have a honeycomb configuration. Consequently, provision may be made according to the invention for the bone replacement to have a so-called micro titanium honeycomb structure.

Preferably, the method further includes a step of checking the bone replacement, after the production thereof, by means of computed tomography (CT), magnetic resonance imaging (MRI) or digital video tomography (DVT). Using this, it is possible to check whether the bone replacement was produced correctly before it is supplied to a medical practitioner or inserted into a patient. Unnecessary treatments with faulty bone replacements and the stress for the patient connected therewith, and the risk of further damage, can be advantageously avoided in this way. It should be mentioned that it is also possible to use other procedures for checking the bone replacement to the ones just mentioned above. In particular, it is possible to use the same procedure for checking the bone replacement as is also used for measuring the cavity. This may save apparatus-based outlay.

Preferably, the method further includes a step of after-treatment of the bone replacement after the production thereof, to be precise, in particular, depending on a check, and in particular at a jawbone region, at a tooth root region or at a gingiva contact region. By way of example, the after-treatment can be effectuated depending on, or in response to, the check of the bone replacement. By way of example, identified faults in the bone replacement can be corrected, in particular by ablating excessive material or by adding missing material. This allows an even better fit of the bone replacement to the cavity, even in the case of processing faults which may occur within the scope of the production process.

According to an embodiment, the bone replacement is a tooth implant or has a tooth implant. This corresponds to a typical and frequent application as teeth must often be wholly or partly replaced on account of various types of damage. Moreover, the method is particularly advantageous in this case since the time which is required for producing the bone replacement and during which a patient may optionally have to live with a gap in the teeth or a temporary appliance may be minimized.

Preferably, a tooth or tooth replacement situated in the cavity is also measured during the step of measuring the cavity, to be precise, in particular, for the purposes of producing further initial data which are indicative for a structure, in particular a surface, of the tooth. This facilitates an integration of the production of a dental prosthesis into the method procedure. It is advantageously possible to dispense with additional steps or the use of separate devices.

It is understood that a tooth can also be measured independently of the cavity and the data obtained herefrom can be used, for example, for producing a dental prosthesis. In so doing, it is possible to correspondingly resort to the other embodiments and variants described herein.

Further preferably, further processing data are produced on the basis of the further initial data, said further processing data being indicative for an intended structure of a dental prosthesis and/or for an intended structure of a prosthesis crown/bridge absorption component. Such processing data can be used in a manner similar to the processing data already mentioned further above in order to facilitate an automated production, wherein, as mentioned above, a dental prosthesis and/or a prosthesis crown/bridge absorption component are produced in this case. Here, a prosthesis crown/bridge absorption component is understood to mean, in particular, an element which is arranged between a dental prosthesis and a tooth implant and which is embodied to absorb shocks or other actions of force. The further initial data which are indicative for the intended structure of a dental prosthesis can advantageously be produced by means of computer-aided design (CAD). Reference is made to the explanations provided further above in respect of the advantages achievable therewith.

Preferably, the method further comprises a step of producing a dental prosthesis on the basis of the further initial data, wherein the production can be effectuated, in particular, by milling and/or a generative manufacturing method, such as e.g. 3D printing. This facilitates particularly advantageous integration of the production of a tooth implant together with a dental prosthesis, wherein, overall, only a minimum number of processing procedures are required.

In particular, the dental prosthesis may be embodied in integral fashion with the tooth implant. This facilitates a simple production and a stable structure. However, it may also be embodied separately from the tooth implant, which may, for example, facilitate the use of special separate production techniques or the provision of special components between a tooth implant and dental prosthesis.

The method preferably further includes a step of checking the dental prosthesis, to be precise, in particular, by means of computed tomography (CT) or a 3D scan. Hence, it is possible to ensure in a manner similar to what was already described above that the prosthesis was produced correctly before the latter is inserted. Malpractice and the complications connected therewith can be avoided.

Further preferably, the method includes a step of treating the dental prosthesis further, which may, in particular, contain a surface treatment. Here, the further processing preferably includes coating a jawbone and/or gingiva contact region, sterilizing and/or packaging.

By means of a further treatment, in particular in the form of a surface treatment, it is possible to correct a possible processing error such that the desired dental prosthesis is obtained, or can be used, despite certain deficiencies in the production. A jawbone and/or gingiva contact region may, for example, be coated with a porous material which establishes a better connection to the jawbone and/or gingiva. A sterilization can serve to remove or kill pathogens. Packaging can prepare the prosthesis, in particular, for shipment to a medical practitioner, for example by post.

Preferably, the method further includes a step of ascertaining respective types of a number of instruments, in particular surgical instruments, to be precise on the basis of the initial data, the processing data, the presence or lack of a root canal, a design (form) of a tooth implant, a design (form) of an abutment and/or a design (form) of a dental prosthesis. This facilitates the use of the data arising within the scope of the method, or else the use of separate data, in order to simplify the treatment for a medical practitioner to the extent that immediately necessary instruments such as forceps or a drill are selected in advance. Consequently, the medical practitioner need no longer think independently prior to the treatment in respect of which instruments he requires for the treatment. By way of example, a certain toolset can be selected for the case where a root canal is present or is intended to be processed. It is likewise possible to take the design into account, for example in respect of dimensions or surface conditions, in order to use tools that are suitable to this end.

Preferably, the method further includes a step of ascertaining navigation information, to be precise, in particular, in relation to a mandible or a maxilla. This step may be based, in particular, on the initial data, the processing data, a root canal, a design of a tooth implant, a design of an abutment and/or a design of a dental prosthesis. Such navigation information may be pre-manufactured information for the medical practitioner, simplifying the treatment for the latter such that said medical practitioner immediately knows, for example, the position on the body or on a jaw at which treatment should be effectuated. The navigation information can also be prepared in such a way that it can be immediately processed further in electronic form, for example for an augmented reality system. By way of example, the medical practitioner may use spectacles or a head-up display which facilitates the superposition of such navigation information. This facilitates guiding and informing the medical practitioner during the treatment, without the latter having to interrupt the treatment in order to look up information.

The invention furthermore relates to a bone replacement which is produced or producible according to a method according to the present invention.

In order to avoid repetition, reference is made to the entirety of the previous description in respect of further features and advantages of the bone replacement. The explanations made there in respect of the bone replacement apply correspondingly.

BRIEF DESCRIPTION OF THE DRAWING

A person skilled in the art will gather further features and advantages from the exemplary embodiments which are described below with reference to the attached drawings.

In the drawings.

DETAILED DESCRIPTION OF THE EXEMPLARY EMBODIMENTS

Figure 1:
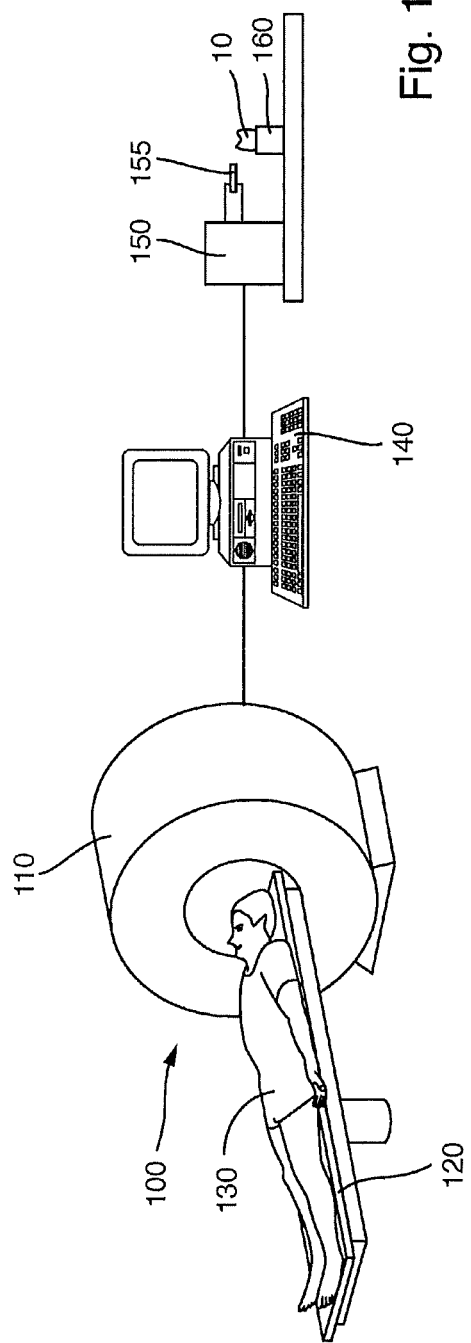
FIG. 1: shows a system for the automated production of a bone replacement.

FIG. 1 shows a system 100 for producing a bone replacement 10.

The system 100 has a computed tomography (CT) scanner 110. A couch 120, on which a patient 130 lies in the present case, is arranged in front of said computed tomography scanner. The couch 120 can be inserted into the computed tomography scanner 110 such that the patient 130 can be examined by means of the computed tomography scanner 110. In particular, this allows the measurement of a cavity in a bone of the patient 130, for which a bone replacement is intended to be produced. In particular, this can be used to measure a cavity for receiving a tooth and also the tooth situated therein.

The system 100 further comprises a computer 140 which is connected to the computed tomography scanner 110 for the purposes of receiving data. Depending on its measurement of the patient 130, the computed tomography scanner 110 produces initial data which are supplied to the computer 140. Said data may be both indicative for a cavity in a bone of the patient 130 and indicative for a bone to be imitated, for example a tooth for which a prosthesis is intended to be produced. It should be noted that the computed tomography scanner 110 may also be controlled by the computer 140.

The computer 140 is configured to convert the initial data into computer-aided design (CAD) data. These CAD data may be displayed to a user such that the latter can carry out a check which prevents subsequent processing steps from using incorrect data.

A so-called 3D volume model, i.e. a virtual model, of the bone replacement is produced for the CAD processing. The 3D volume model is usually used in a CAD program as a construction basis for the design of a new 3D model. However, the 3D model may be modified also in the present form or by being complemented with further 3D models from data libraries.

Depending on the CAD data, the computer 140 subsequently produces processing data which specify how a bone replacement is intended to be produced. When producing the processing data, parameters such as the type of cavity and the position of the cavity in the body of the patient 130 are also taken into account.

Subsequently, a finite element analysis is applied to the processing data. Here too, data in respect of the position of the cavity in the body of the patient 130 and data in respect of a possible occlusion of the cavity and a surrounding bone structure are taken into account.

The produced processing data are subsequently optimized by means of specific algorithms in order to design the subsequent automated processing and use of the processing data to be as efficient and reliable as possible.

Furthermore, the system 100 has a machine tool 150. The processing data that are produced and prepared in the computer 140 are supplied to this machine tool 150. The machine tool 150 has a processing tool 155 which, in a manner known per se, is received in the machine tool 150. In particular, this may be a drill or any other material-ablating device.

The system 100 further has a toolholder 160 adjacent to the machine tool 150. Received in the toolholder 160 is a blank of a bone replacement 10 in order to anchor the latter for the processing by means of the tool 155. The machine tool 150 is embodied to produce the bone replacement 10 in a fully automated manner on the basis of the processing data while said bone replacement is held by the toolholder 160.

After the production of the bone replacement 10, the latter may be separately inserted into the computed tomography scanner 110 in order to be checked. To this end, use can be made of, for example, a special holder. Here, once again, appropriate data are produced depending on the measured bone replacement 10, said data being transmitted to the computer 140. The latter compares the actual state to the intended state and decides whether the bone replacement 10 can be used without change,
the bone replacement 10 requires post-processing, or
the bone replacement 10 was produced so badly that it cannot be used and must be disposed of.

In the case where post-processing is necessary, the computer 140 is able to produce appropriate processing data for the machine tool 150, said data allowing automated post-processing of the bone replacement 10. The bone replacement 10 can then be inserted anew into the toolholder 160 for post-processing purposes.

Figure 2:
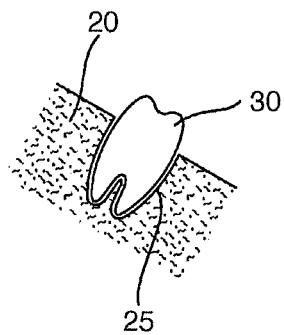
FIG. 2: shows gingiva with a cavity and a tooth.

FIG. 2 shows a portion of gingiva 20 with a cavity 25 formed therein. It is understood that the structure of the gingiva 20 is set by a jawbone which is covered by the gingiva 20. Thus, the cavity 25 is also received in the jawbone. A tooth 30 or tooth replacement 30 is received in the cavity 25. It should be noted that this can be, in particular, natural gingiva 20 and a natural tooth 30. By way of example, the apparatus 100 shown in FIG. 1 can be used to measure the cavity 25 and/or the tooth or tooth replacement 30 and hence produce a replacement for the tooth or tooth replacement 30, said replacement being provided in the form of a bone replacement 10 and fitting exactly into the cavity 25.

Figure 3:
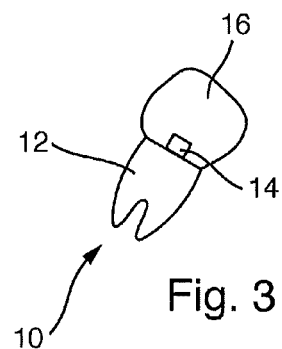
FIG. 3: shows a first exemplary embodiment of a bone replacement.

FIG. 3 shows an exemplary embodiment of a bone replacement 10 in the form of an artificial tooth. Here, the tooth is subdivided into a tooth implant 12, a dental prosthesis and a prosthesis crown/bridge absorption component 14 that connects the tooth implant 12 and the dental prosthesis 16. These three constituent parts 12, 14, 16 of the tooth 10 can all be produced separately in an automated manner by means of the apparatus 100. As already mentioned further above, it is possible to measure a cavity 25, as a result of which, in particular, the structure of the tooth implant 12 is set. It is likewise possible to measure the structure of a tooth 30, in particular the surface structure thereof, in the computed tomography scanner 110 in order to set the structure of the dental prosthesis 16. The prosthesis crown/bridge absorption component 14 can be produced in an automated manner, or else manually, at the computer 140.

Figure 4:
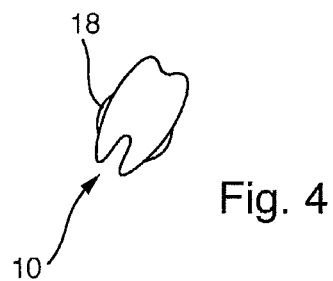
FIG. 4: shows a second exemplary embodiment of a bone replacement.

FIG. 4 shows a bone replacement 10 which is embodied as an integral tooth or tooth replacement. The separation into individual constituent parts, explained with reference to FIG. 3, is consequently not effectuated. Instead, the tooth or the tooth replacement can be produced in one operation from a blank or material by means of the machine tool 150.

In order to improve the adhesion in the jawbone and/or gingiva and in order to improve the growing together with the jawbone and/or gingiva, a coating 18 is applied to the jawbone and/or gingiva contact region of the tooth. This is a porous coating into or onto which the jawbone and/or the gingiva can grow. Such a coating 18 can be applied, in particular, after/during the processing by means of the system 100, for example within the scope of a chemical process.

It should be mentioned that, in parallel with the processing data, the computer 140 can also, in particular, produce data in respect of medical instruments to be used and in respect of navigation data. This simplifies the provision of the instruments necessary for an intervention for a treating medical practitioner and also facilitates, for the latter, the use of advanced navigation and assistance devices such as e.g. spectacles or a head-up display with the option of superimposing appropriate information. Such embodiments may also be referred to as augmented reality.

The invention claimed is:

1. A method for producing an artificial tooth or tooth implant, an abutment and/or a dental prosthesis and for treating a cavity in a mandible or maxilla with the artificial tooth or tooth implant, abutment and/or dental prosthesis, wherein the method includes the following steps conducted by a computer:
   measuring the cavity and producing initial data indicative of a structure of the cavity;
   producing processing data from the initial data, wherein the processing data is indicative of an intended structure of the artificial tooth or tooth implant, abutment and/or dental prosthesis;
   producing the artificial tooth or tooth implant, abutment and/or dental prosthesis by automated processing using the processing data;
   producing surgical instrument data indicative of at least one type of surgical instrument necessary for treating the cavity on the basis of the initial data, the processing data, a root canal, a design of the artificial tooth or tooth implant, a design of the abutment and/or a design of the dental prosthesis; and
   indicating at least one type of surgical instrument necessary for treating the cavity based on the surgical instrument data;
   wherein after the step of indicating, the method further includes treating the cavity with the artificial tooth or tooth implant, abutment and/or dental prosthesis with the at least one type of surgical instrument indicated as necessary for treating the cavity.

2. The method as claimed in claim 1, wherein the cavity is arranged in the mandible or maxilla for receiving a tooth root.

3. The method as claimed in claim 1, wherein the step of measuring the cavity is carried out while a tooth, a tooth replacement, a tooth root or a tooth root replacement is situated in the cavity.

4. The method as claimed in claim 1, wherein the step of measuring the cavity is carried out using computed tomography, magnetic resonance imaging or digital video tomography.

5. The method as claimed in claim 1, wherein the initial data is converted into computer-aided design data by the computer and the processing data is produced on the basis of the computer-aided design data by the computer.

6. The method as claimed in claim 1, wherein the processing data is produced by the computer depending on the cavity and/or a position of the cavity in the mandible or maxilla.

7. The method as claimed in claim 1, wherein a finite element analysis is applied to the processing data by the computer before producing the artificial tooth or tooth implant, abutment and/or dental prosthesis.

8. The method as claimed in claim 7, wherein the finite element analysis applied to the processing data by the computer is carried out taking account of data pertaining to the maxilla, the mandible, occlusion and/or bone structure.

9. The method as claimed in claim 1, including a step of optimizing and/or redesigning the processing data with the computer before producing the artificial tooth or tooth implant, abutment and/or dental prosthesis.

10. The method as claimed in claim 1, including a step of checking the artificial tooth or tooth implant, abutment and/or dental prosthesis, after the production thereof, using computed tomography, magnetic resonance imaging or digital video tomography.

11. The method as claimed in claim 1, including a step of after-treatment of the artificial tooth or tooth implant, abutment and/or dental prosthesis after the production thereof with the computer based on a check at a root region or at a gingiva contact region.

12. The method as claimed in claim 1, wherein the artificial tooth or tooth implant, abutment and/or dental prosthesis is a tooth implant or has a tooth implant.

13. The method as claimed in claim 12, wherein a tooth or the tooth implant situated in the cavity is also measured with the computer during the step of measuring the cavity for the purpose of producing further initial data indicative of a structure of the tooth or the tooth implant.

14. The method as claimed in claim 13, wherein the structure of the tooth or the tooth implant is a surface of the tooth or the tooth implant.

15. The method as claimed in claim 13, including a step of producing further processing data with the computer on the basis of the further initial data, said further processing data being indicative of an intended structure of the dental prosthesis and/or for an intended structure of a prosthesis crown/bridge absorption component.

16. The method as claimed in claim 15, wherein the further initial data is produced by computer-aided design.

17. The method as claimed in claim 15, including a step of producing the dental prosthesis on the basis of the further initial data with the computer.

18. The method as claimed in claim 17, wherein the dental prosthesis is embodied in an integral fashion with the tooth implant or separately from the tooth implant.

19. The method as claimed in claim 17, including a step of checking the dental prosthesis after the production thereof.

20. The method as claimed in claim 19, wherein the step of checking the dental prosthesis includes using computed tomography or a 3D scan.

21. The method as claimed in claim 17, including a step of treating the dental prosthesis further with a surface treatment with the computer.

22. The method as claimed in claim 21, wherein the surface treatment includes coating a jawbone or gingiva contact region of the dental prosthesis, sterilizing the dental prosthesis and/or packaging the dental prosthesis.

23. The method as claimed in claim 17, wherein the step of producing the dental prosthesis includes milling and/or a generative manufacturing method.

24. The method as claimed in claim 1, wherein the step of producing surgical instrument data is carried out on the basis of the initial data and/or the processing data.

25. The method as claimed in claim 1, including a step of ascertaining navigation information with the computer.

26. The method as claimed in claim 25, wherein the step of ascertaining navigation information includes ascertaining navigation information in relation to the mandible or the maxilla on the basis of the initial data, the processing data, a root canal, a design of the artificial tooth or tooth implant, a design of the abutment and/or a design of the dental prosthesis.

27. The method as claimed in claim 1, further including the steps of:
   checking the artificial tooth or tooth implant, abutment and/or dental prosthesis after the production thereof and producing check data;
   comparing the check data with the processing data indicative of the intended structure of the artificial tooth or tooth implant, abutment and/or dental prosthesis; and determining whether the produced artificial tooth or tooth implant, abutment and/or dental prosthesis can be used, requires post-processing or requires disposal.

28. The method as claimed in claim 27, further including:

determining that the produced artificial tooth or tooth implant, abutment and/or dental prosthesis requires post-processing;

producing post-processing data indicative of further processing steps required to be carried out on the produced artificial tooth or tooth implant, abutment and/or dental prosthesis; and further processing the produced artificial tooth or tooth implant, abutment and/or dental prosthesis using the post-processing data.

\* \* \* \* \*